(12) United States Patent
Daly

(10) Patent No.: US 6,427,529 B1
(45) Date of Patent: Aug. 6, 2002

(54) INSTRUMENT FOR SURVEYING THE DEPTH AND VOLUME OF OIL AND BRINE IN A STATIC FLUID COLUMN OF AN OIL WELL

(75) Inventor: LeGrand A. Daly, Houston, TX (US)

(73) Assignee: L.A. Daly Company, Park City, UT (US)

( * ) Notice: Subject to any disclaimer, the term of this patent is extended or adjusted under 35 U.S.C. 154(b) by 0 days.

(21) Appl. No.: 09/675,923

(22) Filed: Sep. 29, 2000

(51) Int. Cl.$^7$ .................. E21B 47/022; G01N 33/18; G01K 1/12; G01D 9/042
(52) U.S. Cl. ................. 73/152.01; 73/152.28; 73/152.42; 73/152.55; 73/61.51; 73/309
(58) Field of Search .............. 73/152.01, 61.43, 73/61.41, 61.51, 304 R, 309, 152.18, 152.28, 152.55, 152.42

(56) References Cited

U.S. PATENT DOCUMENTS

| | | | | |
|---|---|---|---|---|
| 2,776,564 A | * | 1/1957 | Montgomery et al. ........ | 73/151 |
| 2,894,200 A | * | 7/1959 | Szasz ......................... | 324/10 |
| 3,022,826 A | * | 2/1962 | Kisling, III ................. | 166/100 |
| 3,086,167 A | * | 4/1963 | Chaney et al. ................ | 324/1 |
| 3,374,341 A | * | 3/1968 | Klotz ......................... | 235/193 |
| 4,259,975 A | * | 4/1981 | Kinsey, Jr. et al. ............. | 137/1 |
| 5,584,578 A | * | 12/1996 | Clauss, Jr. ................... | 374/140 |
| 5,612,490 A | * | 3/1997 | Carlson et al. ............ | 73/61.43 |
| 5,804,713 A | * | 9/1998 | Kluth ....................... | 73/152.01 |
| 5,804,743 A | * | 9/1998 | Vroblesky et al. ....... | 73/863.23 |
| 5,926,024 A | * | 7/1999 | Blount et al. ............... | 324/324 |
| 5,942,440 A | * | 8/1999 | Dooley et al. .............. | 436/146 |
| 6,209,391 B1 | * | 4/2001 | Dallas ..................... | 73/152.46 |

\* cited by examiner

*Primary Examiner*—Hezron Williams
*Assistant Examiner*—David J. Wiggins
(74) *Attorney, Agent, or Firm*—R. Tracy Crump

(57) ABSTRACT

An instrument and method for surveying the static fluid column of a cased oil well and measuring the volume of oil and brine in the fluid column is disclosed. The instrument uses the inherent differences in specific gravity between water, oil and brine to provide a more simple, convenient, portable and cost effective means for surveying oil columns in cased oil wells. The instrument includes a probe, and a modified fishing rig used to lower and raise the probe into the oil well. The fishing rig includes a handled rod, a reel with a numeric line counter, and length of fused braided fishing line. The numeric line counter visually indicates the length of line expelled from the reel's spool. The probe includes a tubular casing, which is filled with ordinary tap water. The probe is constructed and filled with water so that it has a specific gravity greater than oil and less than brine (approximately 1.0 g/cc).

8 Claims, 2 Drawing Sheets

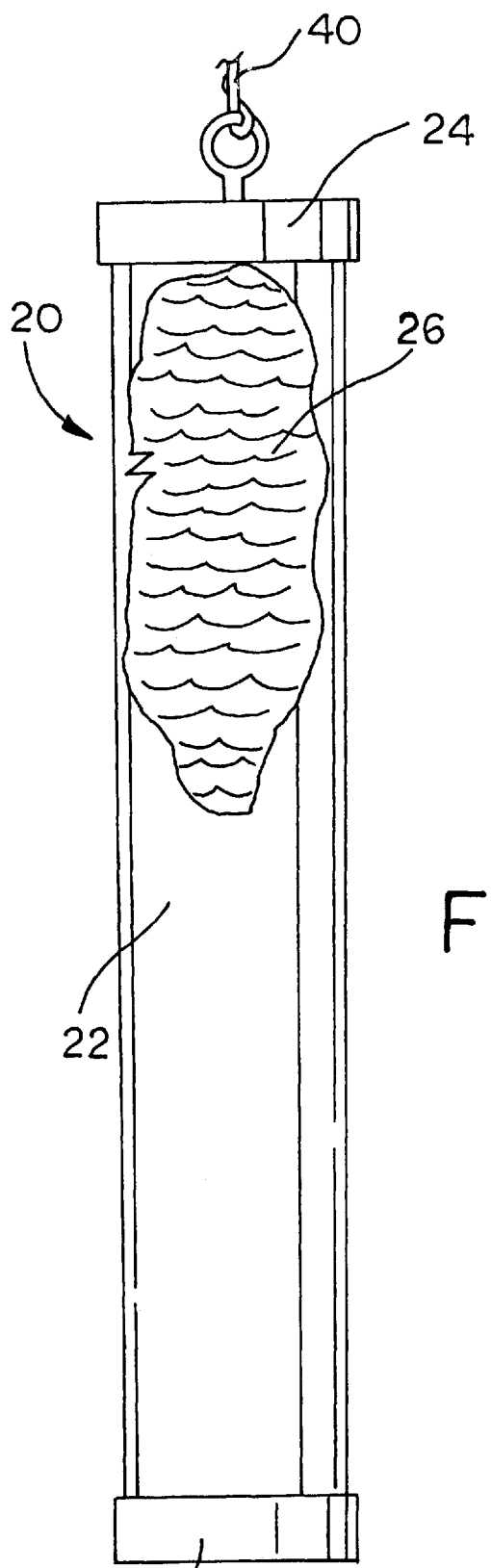
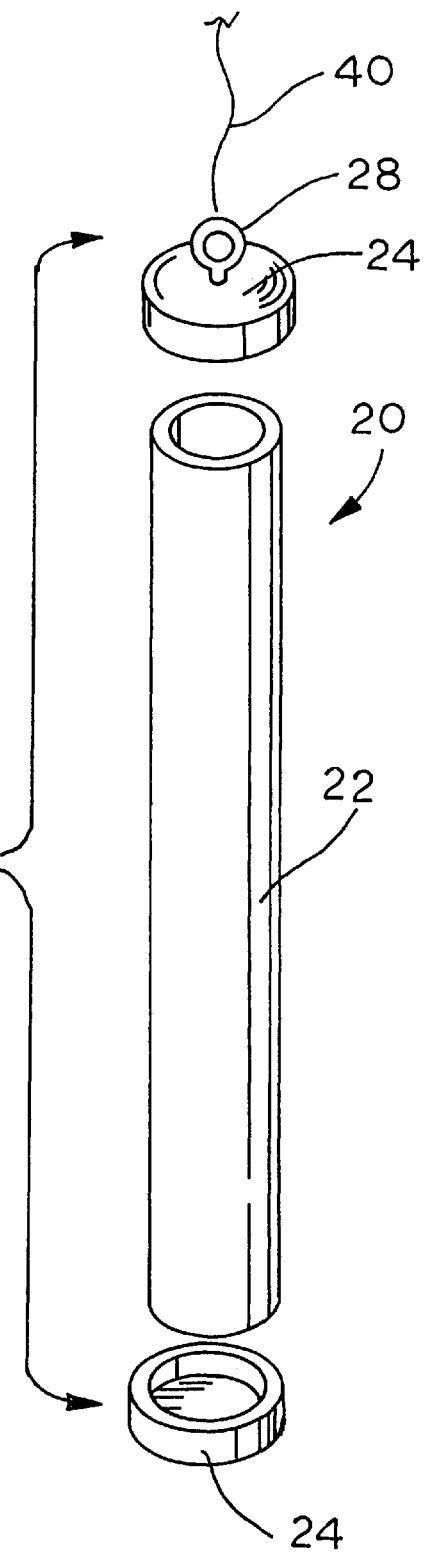
FIG. 2
FIG. 3

INSTRUMENT FOR SURVEYING THE DEPTH AND VOLUME OF OIL AND BRINE IN A STATIC FLUID COLUMN OF AN OIL WELL

This invention relates to an apparatus for surveying the depth and volume of oil and brine in the static fluid column of an oil well.

BACKGROUND OF THE INVENTION

The volume of oil and brine inside cased wells varies greatly. It is often desirable for oil producers to survey and measure the volume and depth of the oil column in any given cased oil well. It is well known that water is heavier than oil (oil floats on water) and brine is heavier than water due to the specific gravity of each medium. "Specific gravity" is the ratio of mass of a,solid or liquid to the mass of an equal volume of distilled water at 4° C.). The specific gravities of water, oil and brine are well known to those skilled in the art. Water has a specific gravity of 1.0 g/cc. Oil has a specific gravity less than water ranging between 0.7 and 0.95 g/cc, and oil brine has a specific gravity of greater than water approximately, 1.3 g/cc. Consequently, the oil column always sits atop the brine column in any cased oil column. The principle problem in surveying the oil column and measuring the volume of oil in a cased oil well is in distinguishing between the oil and brine and at what depth the oil stops and the brine begins.

Heretofore, sophisticated electronic equipment have been used to survey and measure the oil in the static fluid columns of cased oil wells. Conventional surveying equipment uses the difference in electrical capacitance between the oil and brine to survey the fluid column in the oil well. The conventional electronic surveying equipment includes an instrument pack and sensor probe connected to the instrument pack by a long length of electrical wiring. The instrument pack sends an electrical signal to the probe and monitors the change in capacitance sensed by the probe at different depths in the well. The corrosive environment within the fluid column of an oil well is hard on the delicate electrical sensors of the probe. Most importantly, this type of surveying equipment is expensive, complicated and impractical for frequently monitoring multiple oil wells. A simple and inexpensive alternative is desirable.

SUMMARY OF THE INVENTION

The surveying instrument of this invention and its method of use utilizes the inherent differences in specific gravity between water, oil and brine, rather than the difference in electrical capacitance to provide a more simple, convenient, portable and cost effective means for surveying and measuring the volume of oil and brine in the static fluid columns of cased oil wells. The instrument includes a probe, and a modified fishing rig used to lower and raise the probe into the oil well. The fishing rig includes a handled rod, a reel with a numeric line counter, and a length of fused braided, non-stretch fishing line. The numeric line counter visually indicates the length of line expelled from the reel's spool. The probe includes a tubular casing, which is filled with ordinary tap water. The probe is constructed and filled with water so that it has a specific gravity greater than oil and less than brine (approximately 1.0 g/cc).

The instrument is used by simply lowering the probe down the oil well and monitoring its rate of descent via the line counter. The probe will descent rapidly through the air zone of the well. Once the probe reaches the top of the oil column and enters the oil, the probe will continue to descend down the well because of oil's higher specific gravity, but at a noticeably slower rate. Once the change in the rate is detected, the operator records a depth reading from the counter, which marks the depth of the top of the oil column. The probe will stop at the top of the brine column, because the specific gravity of the brine is greater than that of the probe. Once the probe stops, the operator records a second depth reading from the counter, which marks the bottom of the oil column and the top of the brine column. The difference between the first and second readings provides the height of the oil column. From the height of the oil column and the diameter of the well bore, the volume of oil in the column can be easily calculated. If the well depth is known, the volume of the brine column can also be extrapolated.

Accordingly, an advantage of the instrument of this invention and its method of operation is that it utilizes the inherent differences in specific gravity between water, oil and brine to provide a more simple, convenient, portable and cost effective means for surveying and measuring the volume of oil and brine in the static fluid columns of cased oil wells.

Another advantage of this invention is that the instrument eliminates the complex and delicate electrical circuitry of conventional electronic surveying equipment.

Another advantage of this invention is that the instrument is durable and reused, whereas, the delicate electrical sensor probes of conventional equipment must be painstakingly maintained and frequently replaced.

Another advantage of this invention is that the instrument is inexpensive, compact and portable.

Another advantage of this invention is that the instrument can be used by operators with relatively little training and sophistication.

Another advantage of this invention is that a single operator uses the instrument to survey multiple wells in an oil field in a relatively short amount of time and at a fraction of the cost of using conventional electronic equipment.

Other advantages will become apparent upon a reading of the following description.

BRIEF DESCRIPTION OF THE DRAWINGS

A preferred embodiment of the invention has been depicted for illustrative purposes only wherein:

FIG. 2 is a side view of the probe with a portion cut away to reveal the distilled water therein; and FIG. 3 is an exploded perspective view of the probe.

DESCRIPTION OF THE PREFERRED EMBODIMENT

Figure 1:
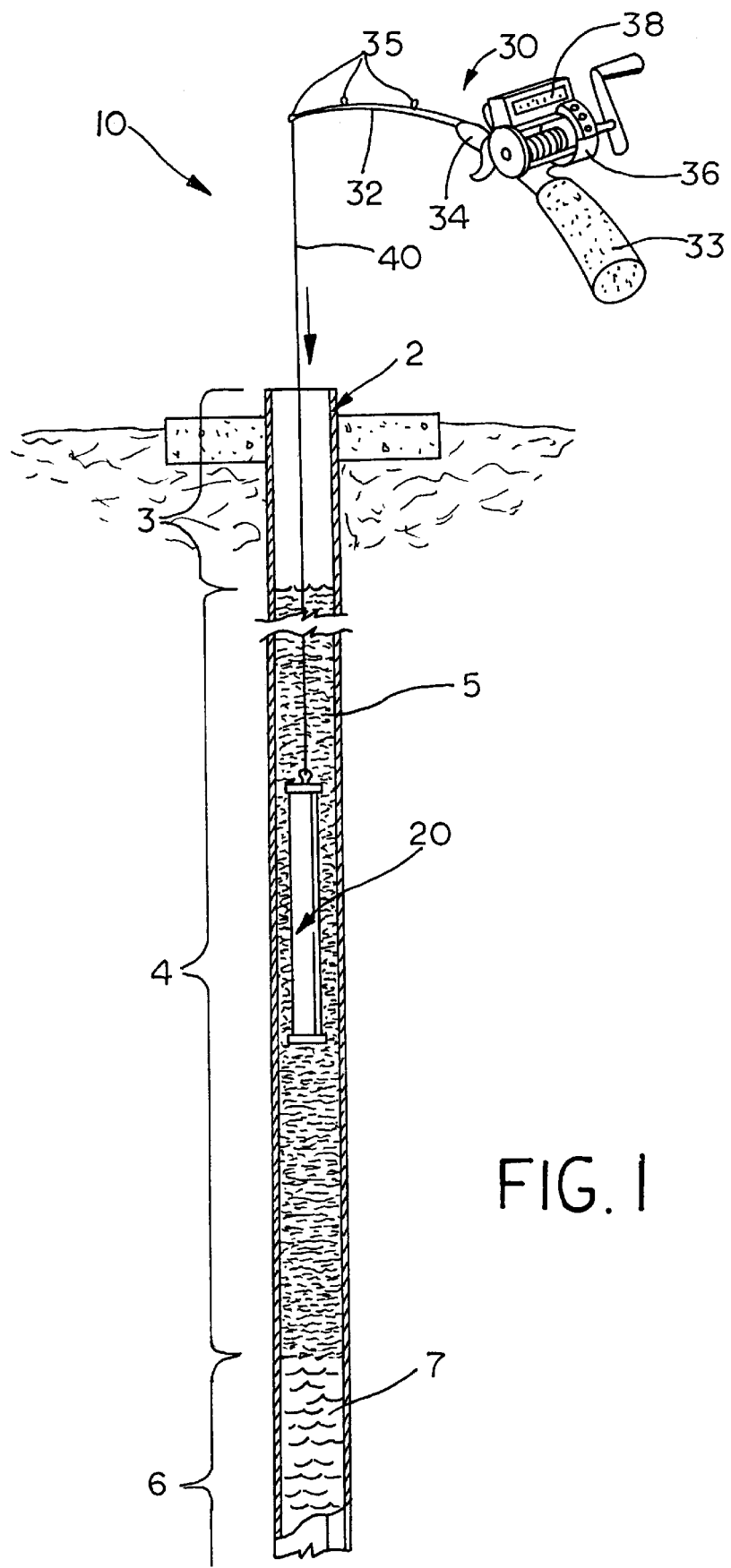
FIG. 1 is a perspective view of the apparatus of this invention illustrating the rod, reel with digital gauge, cable and probe lowered into a cased oil well, which is shown in a side sectional view.

The preferred embodiment herein described is not intended to be exhaustive or to limit the invention to the precise form disclosed. It is chosen and described to best explain the invention so that others skilled in the art might utilize its teachings.

FIG. 1 shows the surveying instrument 10 of this invention. Instrument 10 includes a probe 20, and the modified fishing rig 30 used to lower and raise the probe into the oil well. Rig 30 includes a handled rod 32, reel 36 with a numeric line counter 38, and line 40. Generally, the rod, reel and line are conventional fishing tackle, which are selected and/or modified for application in surveying and measuring the volume of oil and brine in the static fluid columns of cased oil wells. As shown, rig 30 is used in the same manner as conventional fishing tackle to raise and lower probe 20 into the well. Rod 32 is a conventional handled fishing rod, but has been shorted for more convenient storage, transportation and use. As shown, rod 32 has a pistol grip handle 33, fore grip 34 and guides 35 (the end guide preferably being a roller guide) for retaining line 40. Reel 36 is of conventional design and operation, such as the Penn Model #895 manufactured by Penn Reels of Renfrewshire, Scotland. As shown, reel 36 includes a numeric counter line counter 38., which visually indicated the length of line expelled from the spool. As illustrated in FIG. 1, counter 38 has an electronic display, such as an LED (Light emitting diode) or LCD (liquid crystal display) display. Although electronic displays are illustrated, any mechanical or electro-mechanical mechanism, which visually displays the length of line expelled from the reel may be employed. As set forth and explained in detail hereafter, readings from counter 38 are important to the instrument and methodology of this invention. In addition, reel 36 may have a drag mechanism (not shown) to provide resistance to the line as it is spooled from the reel. This is a convenient feature for use in the present invention. Line 40 is a conventional non-stretching fused Kevlar Triline of sufficient counter and strength to support the weight of probe 20, such as the braided line manufactured and sold by Berkley of Spirit Lake, Iowa under the trademark, Trilene. A length of line 40 sufficient to reach the entire depth of an oil column is wound onto the spool of reel 36.

Probe 20 includes tubular casing 22 and two end caps 24, which are constructed of PVC (polyvinyl chloride) plastic. End caps 24 enclose and hermetically seal casing 22, which is filled with water 26. One end cap has an eyelet 28 to which line 40 is connected. The dimensions of probe 20 are selected so that the specific gravity of the probe is approximately 1.0 g/cc. One skilled in the art will note that PVC has a specific gravity between 1.3-1.45 g/cc, while water has a specific gravity of 1.0 g/cc. Consequently, the length and diameter of probe 20 is selected, such that the volume of the PVC casing and end caps is significantly less than the volume of water contained therein. As such, the specific gravity of probe 20 is only marginally higher than the water contained in the casing, and is significantly more than oil and significantly less than brine. Generally, the probe is less than three (3) feet long and is less than two (2) inches in diameter. The compact dimensions of probe 20 allows instrument 10 to be easily carried and stored for field use. While, casing 22 and end caps 24 are described herein as constructed of PVC plastic, they may be constructed of any suitable oil resistant material so as that the specific gravity of the probe remains approximately 1.0 g/cc.

FIG. 1 illustrates the operation of apparatus 10 as used to survey and measure the volume of oil and brine in a static fluid column of a cased oil well 2. With probe 20 connected to line 40 of rig 30, the probe is lowered into well 2. As probe 20 descends, counter 38 displays the amount of line unwound from the reel. The operator can visually monitor the rate at which probe 20 descends down well 2. In addition, the user can "thumb" the reel, that is feel the line as it is pulled from the reel to tactically monitor the rate of descent. Probe 20 will descend rapidly through air zone 3 of the well. In the air zone, where the specific gravity of air is zero, the probe descends at the maximum rate permitted by the user's "thumb" and the resistance in the reel. The rate of descent through air zone 3 can also be adjusted by the mechanical drag of reel 34 if desired to monitor the rate of descent.

Once the probe reaches the top of the oil column 4 and enters the oil 5, its rate of descent will dramatically slow, but will not stop. The change in the rate of descent is due to the difference in specific gravity between probe 20 and the oil of oil column 4, through which it passes. Once in the oil column, probe 20 will continue to descend because of its higher specific gravity, but at a much slower rate. The change in the rate of descent will be clearly evident to the operator monitoring either the counter or by "thumbing" the reel. Once the change in the rate is detected, the operator records a depth reading from the counter, which marks the depth of the top of oil column 4.

The probe will continue to descend through oil column 4, but will stop at the top of brine column 6. The descent of the probe is halted because the specific gravity of brine 7 is greater than that of the probe. Once the probe stop, the operator records a second depth reading from the counter, which marks the bottom of oil column 4 and the top of brine column 6.

The survey of oil column 4 and measurement of the volume of oil is derived from the two numeric counter readings. The first reading marks the depth of the top of oil column 4 and the second reading marks the bottom of the oil column and the start of brine column 6. The difference between the first and second readings provides the height of oil column 4. From the height of the oil column and the diameter of the well bore, the volume of oil in the fluid column can be easily calculated. If the total well depth is known, the volume of brine can also be calculated.

One skilled in the art will note that instrument 10 and its method of use have several advantages over prior electronic surveying equipment. By utilizing the inherent differences in specific gravity between water, oil and brine, instrument 10 provides a more simple, convenient, portable and cost effective means for surveying oil and brine columns in cased oil wells. Instrument 10 and its methodology eliminates the complex and sensitive electrical circuitry of conventional electrical surveying equipment, which detects differences in electrical capacitance between the mediums. Unlike conventional electrical survey equipment, instrument 10 can be used by a single operator with little if any training. Probe 20 is durable and reused, whereas, the delicate electrical sensor probes of conventional equipment must be painstakingly maintained and frequently replaced. The cost of the fused braided line of this invention is significantly more cost effective than the electrical wiring that must be connect to the electrical probes of conventional survey equipment.

In addition, the simple construction and operation of Instrument 10 is more cost effective and practical for use in the oil fields. The plastic construction not only makes the probe durable and light weight, but makes it easily cleaned after use by wiping off the excess oil. The probe 20 and rig 30 are compact and easily portable by an operator from well to well. In addition, survey instrument 10 can be conveniently stored behind and under the seats of truck-cabs. A single operator can survey multiple wells in an oil field in a relatively short amount of time and at a fraction of the cost of surveying using conventional electronic equipment.

It is understood that the above description does not limit the invention to the details given, but may be modified within the scope of the following claims.

I claim:

1. An apparatus for surveying a static fluid column, which contains an oil column and a brine column, in a cased oil well, and for measuring the volumes of an oil in the oil column and a brine in the brine column, the apparatus comprising:

probe means for emersion through the oil column within the well at an observed rate of descent over a series of depths and with the probe means having a specific gravity greater than the oil but less than the brine, means for raising and lowering the probe means in the well, whereby the rate of descent of the probe means within the well when lowered into the well will noticeably slow once the probe means enters the oil column and will stop once the probe means encounters the brine column, and means for measuring the depth and rate of descent of the probe means within the well, such that, the depth at which the rate of descent of the probe means slows corresponds to the top of the oil column and the depth at which the rate of the descent of the probe means is zero corresponds to the top of the brine column.

2. The apparatus of claim 1 wherein the probe means includes a tubular vessel and tap water contained within the vessel.

3. The apparatus of claim 1 wherein raising and lower means includes a reel and a length of line wound onto the reel.

4. The apparatus of claim 1 wherein the measuring means includes means for indicating the length of cable unwound from the reel as the probe means is lowered into the well.

5. A method for surveying a static fluid column in a cased oil well with a probe, where the static fluid column contains a column of an oil having an oil height and a column of a brine having a brine height, the method comprising:
   a. Lowering a probe having a specific gravity greater than the oil but less than the brine into the well at an observed rate of descent over a series of depths;
   b. Monitoring the rate of descent of the probe as the probe descends down the well;
   c. Recording a first depth at which the rate of decent of the probe noticeably slows, whereby the first recorded depth corresponds to the top of the oil column;
   d. Recording a second depth at which the probe stops within the well, whereby the second recorded depth corresponds to the top of the brine column; and
   e. Calculating the difference between the first and second recorded depths whereby the difference between the first and second recorded depths corresponds to the oil height of the oil column.

6. The method of claim 5 and the steps:
   f. Determining the total depth of the cased well; and
   g. Calculating the difference between the second recorded depth and the total depth, whereby the difference between the second recorded depth and the total depth corresponds to the brine height of the brine column.

7. A method for measuring the volume of an oil and a brine in a static fluid column of a cased oil well using a probe, where the cased oil well has a cross sectional area A and a total depth D, and the static fluid column contains an oil column having an oil height and a brine column having a brine height, the method for measuring the volume of the oil and the brine comprising the steps:
   a. Lowering the probe having a specific gravity greater than the oil but less than the brine into the well at an observed rate of descent over a series of depths;
   b. Monitoring the rate of descent of the probe as the probe descend down the well;
   c. Recording a first depth at which the rate of decent of the probe noticeably slows, whereby the first recorded depth corresponds to the top of the oil column;
   d. Recording a second depth at which the probe part stops within the well, whereby the second recorded depth corresponds to the top of the brine column;
   e. Calculating the difference between the first and second recorded depths whereby the difference between the first and second recorded depths corresponds to the oil height of the oil column;
   f. Determining the cross-sectional area A of the cased well; and
   g. Calculating the volume of oil in the fluid column, whereby the oil height of the oil column multiplied by the cross-sectional area A of the cased well corresponds to the volume of the oil in the oil column.

8. The method of claim 7 and the steps:
   h. Determining the total depth D of the cased well;
   i. Calculating the difference between the second recorded depths and the total depth D, whereby the difference between the second recorded depths and the total depth corresponds to the brine height of the brine column; and
   j. Calculating the volume of brine in the fluid column, whereby the brine height of the brine column multiplied by the cross-sectional area A of the cased well corresponds to the volume of the brine in the brine column.

* * * * *